(12) United States Patent
Hayzelden

(10) Patent No.: US 7,540,853 B2
(45) Date of Patent: Jun. 2, 2009

(54) METHOD AND APPARATUS FOR DIVERTING BLOOD FLOW DURING ABLATION PROCEDURES

(75) Inventor: Robert Hayzelden, Canyon Lake, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 594 days.

(21) Appl. No.: 10/610,099

(22) Filed: Jun. 30, 2003

(65) Prior Publication Data
US 2004/0267337 A1 Dec. 30, 2004

(51) Int. Cl.
*A61M 29/00* (2006.01)

(52) U.S. Cl. ............... 604/96.01; 607/101; 607/113

(58) Field of Classification Search .......... 604/46, 604/47, 102.01, 101.03, 102.03, 99.02, 96.01; 607/101, 113; 600/434; 128/898; 606/41, 606/198
See application file for complete search history.

(56) References Cited

U.S. PATENT DOCUMENTS

| | | | |
|---|---|---|---|
| 5,971,983 A * | 10/1999 | Lesh | 606/41 |
| 6,012,457 A * | 1/2000 | Lesh | 128/898 |
| 6,159,207 A * | 12/2000 | Yoon | 606/41 |
| 6,161,543 A * | 12/2000 | Cox et al. | 128/898 |
| 6,234,995 B1 * | 5/2001 | Peacock, III | 604/96.01 |
| 6,500,167 B1 * | 12/2002 | Webster, Jr. | 604/528 |
| 2001/0020160 A1 * | 9/2001 | Esch et al. | 604/509 |
| 2001/0049523 A1 * | 12/2001 | DeVore et al. | 606/41 |
| 2002/0002329 A1 | 1/2002 | Avitall | |
| 2002/0062124 A1 | 5/2002 | Keane | |
| 2002/0177765 A1 * | 11/2002 | Bowe et al. | 600/374 |
| 2003/0050637 A1 * | 3/2003 | Maguire et al. | 606/41 |
| 2003/0060821 A1 | 3/2003 | Hall et al. | |
| 2003/0078574 A1 * | 4/2003 | Hall et al. | 606/41 |

\* cited by examiner

*Primary Examiner*—Nicholas D Lucchesi
*Assistant Examiner*—Christopher D Koharski
(74) *Attorney, Agent, or Firm*—Hollingsworth & Funk, LLC

(57) ABSTRACT

A diversion catheter for use during ablation procedures includes a distal occlusion device such as a diversion balloon. The diversion balloon blocks blood flowing through a cardiac vein. The diversion catheter employs ports proximal and distal to the diversion balloon. The proximal and distal ports are in fluid communication so that blood flow through the cardiac vein is diverted through the distal and proximal ports and away from a cardiac surface intended for ablation.

26 Claims, 6 Drawing Sheets

METHOD AND APPARATUS FOR DIVERTING BLOOD FLOW DURING ABLATION PROCEDURES

FIELD OF THE INVENTION

The invention relates generally to catheter systems, and, more particularly, to catheters used for treating heart conditions.

BACKGROUND

Cardiac ablation treatments involve the use of heat or freezing to create lesions in tissue for purposes such as restoring normal functioning of electrical activity near the tissue. Generally, cardiac ablation involves introducing a catheter into the heart where a therapeutic procedure can be carried out on abnormal heart tissue. Radio frequency (RF) ablation catheters employ electrodes at a distal end that can transfer RF or microwave electromagnetic energy to heart tissue. Catheter ablation is often used to treat atrial fibrillation and other types of heart rhythm disorders.

Common ablative treatment areas include the openings (or ostiums) of veins or arteries into chambers of the heart. For example, the ostium of the pulmonary vein is commonly treated by using an ablation catheter in the left atrium. While using an ablation catheter to treat ostium regions, the blood flowing from the vein or artery tends to cool the ablation electrodes. This cooling effect can sometimes make it difficult to deliver sufficient energy to create effective lesions.

Devices exist that can occlude the flow through blood vessels while ablation procedures are performed, and thereby diminishing the cooling effects. However, there are problems associated with occluding major vessels such as the pulmonary vein. Restriction of blood flow in these circulatory passageways for long durations of time can lead to complications in the patient. Therefore, use of full occlusion during ablation or other tissue procedures is necessarily time-limited. If the clinician cannot complete the procedure quickly, the occlusion devices must be regularly checked, engaged, and disengaged to allow some minimal amount of blood flow. This can add time and complexity to the ablation procedure.

SUMMARY

The present disclosure describes a method and apparatus for diverting blood flow around an ablation device. In one embodiment, a diversion catheter includes a catheter body having a proximal end and a distal end. An inflation lumen is in fluid connection with an inflation mechanism situated proximate the proximal end of the catheter body. A diversion balloon is fixably mounted at the distal end of the catheter body and inflatable to at least partially block blood flow through the cardiac vessel. One or more distal ports are provided on the catheter body distal to the diversion balloon. One or more proximal ports are provided on the catheter body proximal to the diversion balloon. The proximal ports are in fluid connection with the distal ports. A flow of blood through the cardiac vessel is directed via the distal and proximal ports so as to divert blood flow from a cardiac surface intended for ablation.

The catheter may include an inner dam situated within the catheter body proximal of the proximal ports, the inner dam blocking the flow of blood into the catheter body beyond the inner dam. In one arrangement, the catheter body includes one or more marker bands to facilitate proper placement of the diversion balloon relative to the cardiac vessel.

In another embodiment of the present invention, a diversion catheter may further include one or more electrical conductors disposed along the catheter body and extending from the proximal end of the catheter body to at least a location proximate the diversion balloon. An arrangement of electrodes is supported by the catheter body. The electrodes are electrically coupled to the one or more electrical conductors. The arrangement of electrodes are operable for one or both of mapping and ablating a cardiac surface while the distal and proximal ports divert blood flow away from the cardiac surface.

In one configuration, the arrangement of electrodes is configured for RF (radio frequency) ablation of the cardiac surface. The arrangement of electrodes may also be configured for microwave ablation of the cardiac surface. The catheter may include a cryogenic element supported by the catheter body. The cryogenic element configured for treatment of the cardiac surface.

In another configuration, the arrangement of electrodes is arranged in a folded configuration. The arrangement of electrodes in the folded configuration substantially conforms to an outer surface of the catheter body. The arrangement of electrodes may be selectably deployable from the folded configuration to a deployed configuration. In the deployed configuration the arrangement of electrodes at least partially conforms to the cardiac surface.

In another embodiment of the present invention, a method of ablating a cardiac surface involves advancing a diversion catheter having a distal diversion balloon at least partially into a cardiac vessel. The diversion balloon is inflated to stabilize the catheter. A majority of cardiac vessel blood flow is diverted through a portion of the diversion catheter and away from the cardiac surface intended for ablation, and the cardiac surface is ablated.

The method may involve using one or more of RF (radio frequency) ablation, cryogenic ablation, and microwave ablation to ablate the cardiac surface. The method may also involve detecting one or more marker bands provided proximate or on the diversion balloon to properly position the diversion balloon relative to the cardiac vessel.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
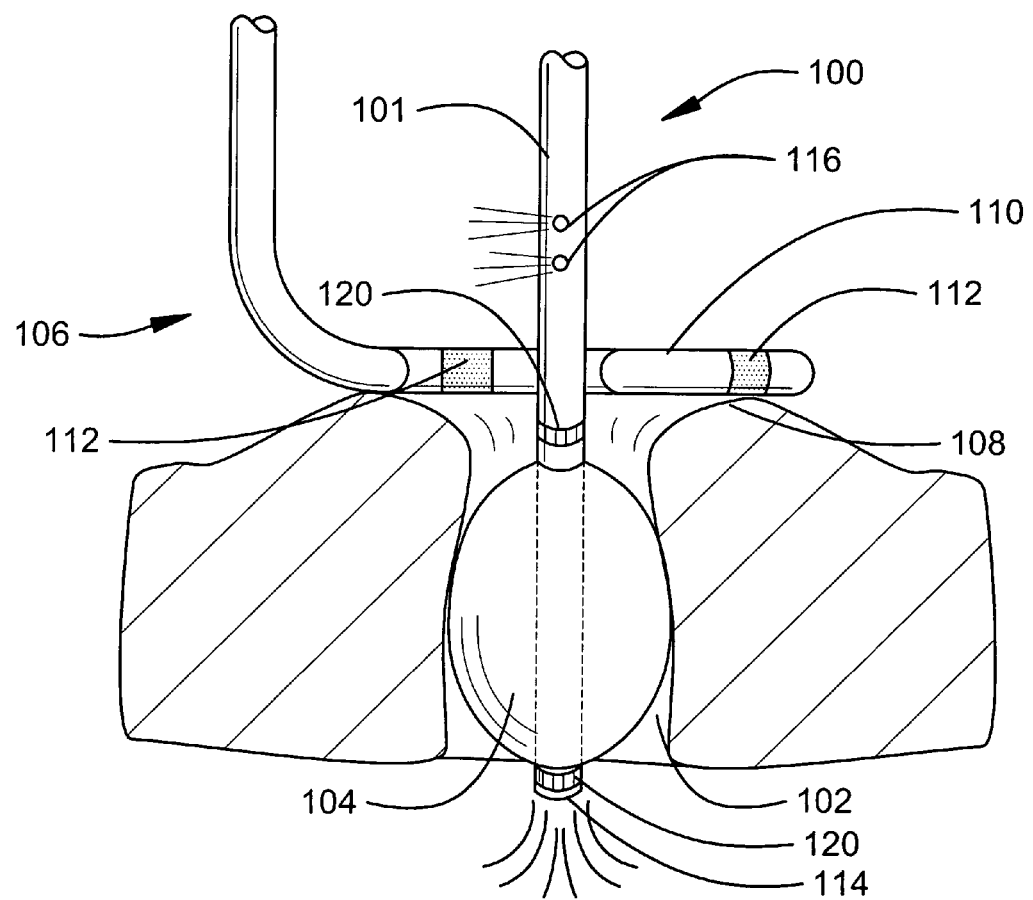
FIG. 1 is a side view of an ablating catheter with a diverting catheter positioned in a blood vessel according to an embodiment of the present invention.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, the present disclosure describes a method and apparatus for diverting blood flow away from areas such as the contact areas of an ablative device. In one embodiment, an apparatus includes a catheter body having a balloon or other occluding device mounted on the distal end. The catheter body includes distal ports that are positioned distal to the occluding device and proximal ports that are proximal the occluding device. The distal ports and proximal ports are in fluid connection so that a flow is diverted away from a cardiac surface intended for ablation.

In reference to FIG. 1, a diverting (or diversion) catheter 100 is illustrated according to an embodiment of the present invention. The diverting catheter 100 is show deployed in a blood vessel 102, such as a pulmonary vein. The diverting catheter 100 includes an elongated body 101 and an occlusion device such as an occlusion/diversion balloon 104 that can restrict blood flow through the vessel 102. The balloon 104 can also function to stabilize the distal part of the diverting catheter 100 in the vessel. The balloon 104 is typically an annular-shaped latex balloon fixably attached to a portion of the catheter 100. However, it will be appreciated that the diverting catheter 100 may employ any manner of occlusion device, such as sponges or a mechanically/hydraulically actuated apparatus that can be employed to selectably block a blood vessel.

The diverting catheter 100 can be used with an ablation device, such as the radio frequency (RF) ablation catheter 106 shown positioned proximate the diverting catheter 100. The ablation catheter 106 is depicted as an electrode tip catheter for delivering RF or microwave energy to tissue. It is understood that the diverting catheter 100 may also be used with other types of tissue treatment catheters, such as cryogenic catheters. In general, the diverting catheter 100 can be used with any tissue treatment apparatus that may experience degraded performance due to local blood flow near the treatment area.

The illustrated ablation catheter 106 includes a loop shaped distal tip 110 with externally mounted electrodes 112. The ablation catheter 106 is arranged to deliver electromagnetic energy to an ostium 108 of the vein 104. The looped shape of the ablation catheter's distal tip 110 allows the ablation catheter 106 to deliver generally ring shaped lesions in the tissue around the ostium 108. The looped shape tip 110 can be centered on the body 101 of the positioned diverting catheter 100.

The balloon 104 of the diverting catheter 100 is arranged to partially or fully block the vessel 102 during ablation procedures. This blocking helps prevents blood from flowing in the area where the electrodes 112 contact the tissue. Reducing blood flow to the electrode contact area during ablation reduces convective cooling effects of the moving fluid, thereby allowing the electrodes 112 to operate more efficiently. Similarly, when used with cryogenic devices, the diverting catheter reduces convective heating effects of blood near the contact area.

Even though the balloon 104 blocks the vessel 102, the diverting catheter 100 can be arranged to permit blood to flow around the blocked section. The diverting catheter 100 includes distal ports 114 and proximal ports 116 that allow blood to continue flowing through the vessel 102 during the procedure while still removing local heat transfer effects at the ostium 108. The distal ports 114 are in fluid connection with the proximal ports 116, thereby allowing fluid to flow between the ports 114, 116 without the fluid impinging on or otherwise cooling the electrodes 112.

The distal ports 114 are positioned distal to the occluding balloon 104 and may include one or more openings at the distal tip of the catheter 100 as shown. The distal ports 114 may also include voids in the side wall of the catheter body 101. The proximal ports 116 are located proximal to the balloon 104, and preferably at a distance from the electrodes 112 to negate the local cooling effects of any fluid that might exit the proximal ports 116. As shown, the proximal ports 116 may include openings in the side wall of the catheter body 101.

The proximal ports 116 are preferably placed to direct a majority of blood flow away from the treatment area. This placement may include using various sized ports 116 arranged on the catheter body 101, with larger ports 116 further away from the treatment area. Similar effects may be obtained by varying the shape and/or exit angle of the ports 116. Size and arrangement of the proximal ports 116 will vary depending on the application, although the ports 116 are generally arranged to direct blood flow away from the surface of cardiac tissue or vasculature subject to treatment.

To assist in properly locating the diverting catheter 100 in the destination vessel 102, the catheter 100 may include markers 120 to help position the balloon 104 in the vessel 102 correctly. These markers 120 may be located anywhere on the diverting catheter 100, including the balloon 104, but the illustrated locations (approximately distal and proximal to the balloon 104) are preferred. The markers 120 may include visual indicators that are readily perceivable using an optical viewing apparatus. The markers 120 may also include radiopaque indicators that are visible on X-ray or other radiographic imaging equipment.

Besides redirecting blood flow, the diverting catheter 100 can provide additional benefits during ablation or similar procedures. For example, the inflated balloon 104 prevents the ablation catheter 106 from entering into the vessel 102 during positioning. The inside of the vessel 102 is typically not a preferred target location for ablation because stenosis may occur if the ablative lesions occur within the vessel 102.

Therefore, the inflated balloon 104 prevents this from occurring by keeping the tip of the ablation catheter 106 out of the vessel 102.

The diverting catheter 100 can also assist in centering the ablation catheter 106 on the ostium 108. Once in position, the body 101 of the diverting catheter 100 acts as guide with which to navigate the loop-shaped tip 110 of the ablation catheter 106. This can help ensure that lesions created by the ablation catheter 106 are properly placed on the ostium 108.

Figure 2:
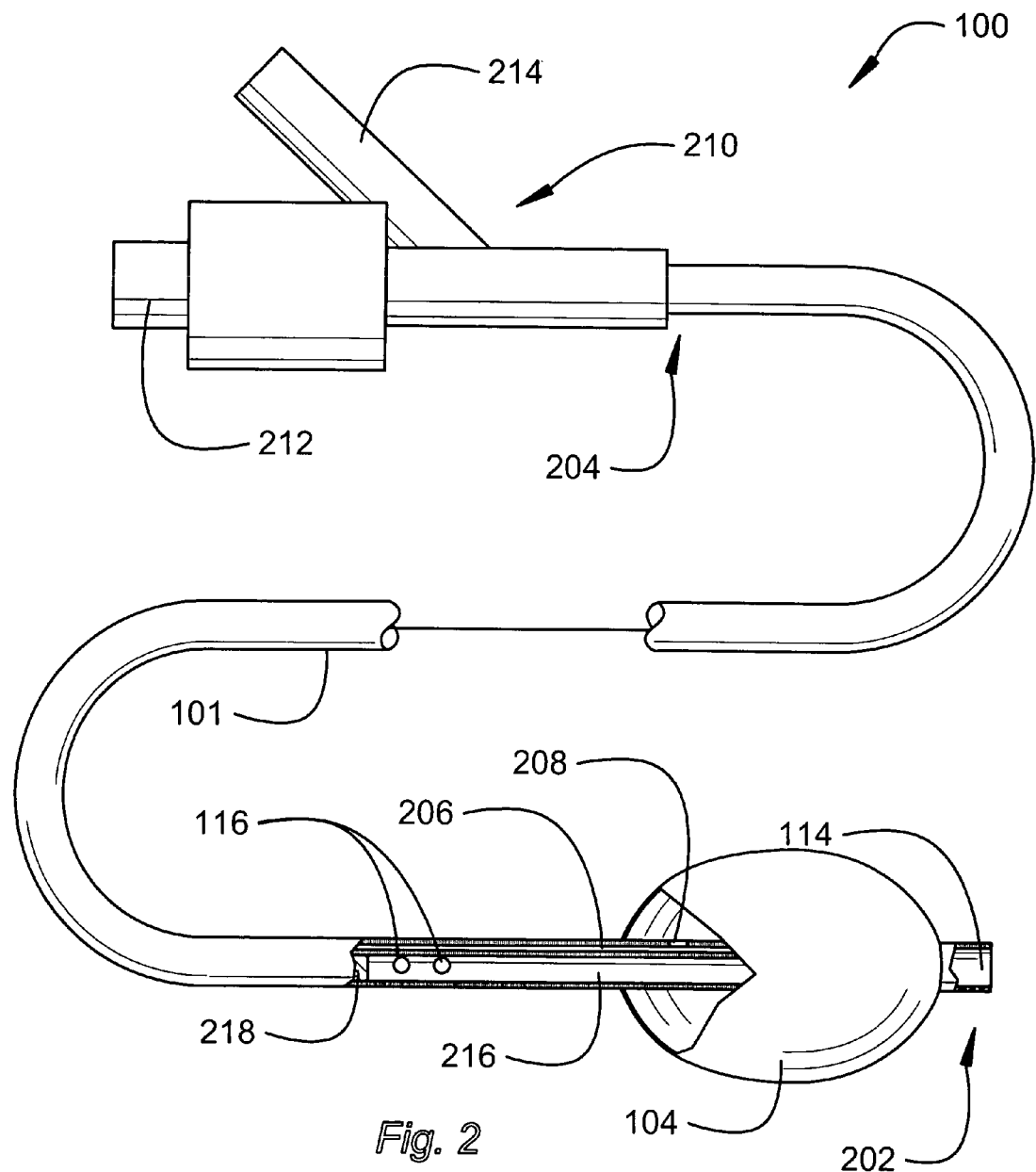
FIG. 2 is a side view of a diverting catheter according to an embodiment of the present invention.

Turning now to FIG. 2, one configuration of a diverting catheter 100 is illustrated according to embodiments of the present invention. The diverting catheter 100 includes an elongated body 101 with distal and proximal ends 202, 204, respectively. The balloon 104 or other occlusion device is positioned near the distal end 202.

The illustrated balloon 104 may include a standard polymer (e.g. latex) inflatable member that is in fluid contact with an inflation lumen 206 and inflation port 208. The inflation lumen 206 can be any internal or externally located fluid passageway extending along the elongated body 101. Fluid can be pressurized in the inflation lumen 206, thereby entering through the inflation port 208 and inflating the balloon 104. A proximal attachment 210 is provided at the proximal end 204 of the elongated body 101 and provides fluid access to the inflation lumen 206 as well as any other lumens or passageways that may be included in the elongated body 101.

The proximal attachment 210 may include one or more luer-type attachments such as an axial port 212 and/or a side port 214. In general, the ports 212, 214 allow for fluid connections with lumens of the elongated body 101. In particular, one or more of the luer ports 212, 214 may be in fluid communication with the inflation lumen 206 for inflating and deflating the balloon 104. Other uses of the ports 212, 214 include providing for flushing of various passages of the elongated body 101, and for passing of an apparatus into the body 101 such as a sensor and/or guide wire.

Referring now to the distal end 202 of the elongated body 101, the distal port(s) 114, and proximal ports 116 are coupled via a bypass lumen 216. In this example, the bypass lumen 216 is formed as a central open lumen of the elongated body. Alternatively, where a plurality of ports 114, 116 are used, a plurality of separate bypass lumens 216 may connect two or more ports 114, 116. An inner dam 218 may be provided in the bypass lumen 216 proximal to the proximal ports 206. The inner dam 218 restricts the blood flow to the distal part of the diverting catheter 100, typically confining blood flow between the distal and proximal ports 114, 116.

In one arrangement, the inner dam 218 may be formed as the distal tip of a slidable inner member. In such an arrangement, the position of the dam 218 may be adjusted so that some parts of the proximal ports 116 are blocked. Using a slidable inner member or similar apparatus to block some of the proximal ports 116 allows the blood flow through the bypass lumen 216 to be selectably controlled. Other bypass flow control mechanisms may include devices such as a pressure relief valve (not shown) that are placed within the bypass lumen 216. Such a pressure relief valve could be set to automatically control flow rate, or may be controllable from a proximal end of the diverting catheter 100.

The diverting catheter 100 as illustrated in FIG. 2 is usable with various ablation/cryogenic devices, although other devices may also be involved in the ablation/cryogenic procedures. For example, a guide apparatus may be used to assist in positioning the diverting catheter 100 and/or ablation catheter 106. The catheters 100, 106 may be introduced via guide apparatuses such as guide wires or guide catheters. The guide apparatus may include steering features that allow maneuvering a distal part of the guide apparatus to the destination vessels.

In another example, the catheters 100, 106 may include a steering apparatus that provides a self-steering capability in addition to, or exclusive of, that provided by a guide apparatus. In situations where the pathway is convoluted, for example, the availability of multiple independent steering guide apparatuses and catheters 100, 106 may assist in locating the treatment area. In other situations, steerable diversion and ablation catheters 100, 106 may be used without other guiding apparatus. This may help to reduce the procedure time needed to prepare and place the catheters 100, 106.

Figure 3:
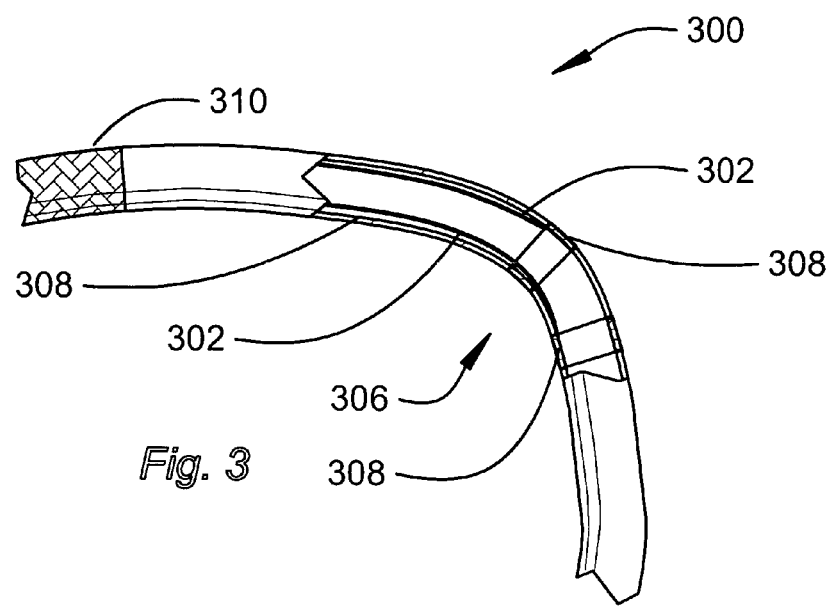
FIG. 3 is a partial cutaway view showing a catheter steering mechanism according to an embodiment of the present invention.

FIG. 3 illustrates a catheter body 300 with an internal steering arrangement. Such a steering arrangement may be employed in both the diversion catheter 100 and the ablation catheter 106. The steering arrangement includes one or more steering tendons 302. The steering tendons 302 may be formed from a metallic or fibrous member. The steering tendons 302 are deployed within the catheter body 300, typically in a dedicated lumen (not shown).

In the illustrated arrangement of FIG. 3, two steering tendons 302 are each fixed to an anchor member 308. In other arrangements, each tendon 302 may be affixed to the same anchor member 308. The anchor members 308 may be bands or plugs, and typically serve as a distal attachment points for the steering tendons 302. The anchor members 308 are located distal to a deflection area 306 of the catheter body 300. The deflection area 306 may be straight or curved in a neutral orientation. When a bi-directional steering arrangement is used, the deflection area 306 is preferably straight in a neutral orientation.

The catheter body 300 is typically formed so that it is relatively flexible in an area encompassing at least part of the deflection area 306. A stiffness transition 310 may be included proximal to the deflection area 306. Thus, when a force is applied to one or more of the steering tendons 302, the catheter body 300 will deflect in a predictable manner, generally deflecting around the deflection area 306.

Figure 4:
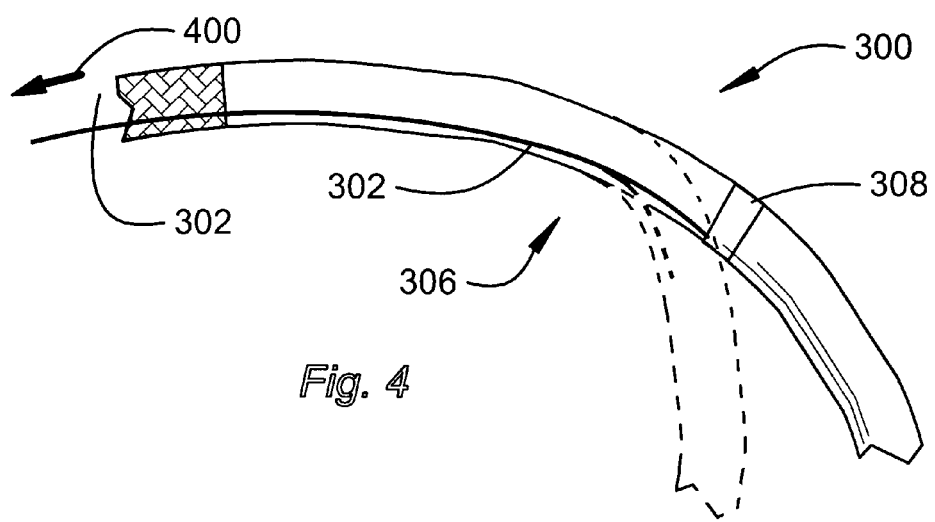
FIG. 4 is a side view of the catheter shaft illustrating steering deflection according to an embodiment of the present invention.

The operation of a steering tendon 302 is illustrated in FIG. 4. The initial shape of the catheter body 300 is shown in dashed lines. The single tendon 302 can be pulled in the direction of the arrow 400, causing the elongated body 101 to deflect to the indicated shape. Steering with a single tendon 302 as shown in FIG. 2 provides unidirectional steering control. When additional tendons 302 are included as shown in FIG. 3, multidirectional steering modes may be provided.

As shown in FIGS. 1-4, the diverting and ablation catheters 100, 106 include features that allow the catheters 100, 106 to be used together. For example, the diverting catheter 100 can act as a guide for positioning the loop-shaped tip 110 of the ablation catheter 106 so that the loop 110 is centered and does not protrude into the vessel 102. One or both of the catheters 100, 106 may include steering apparatus that assist in positioning the catheters 100, 106. It will also be appreciated that features of the diverting catheter 100 and ablation catheter 106 can be combined into a single apparatus. One such apparatus is shown in FIG. 5.

Figure 5:
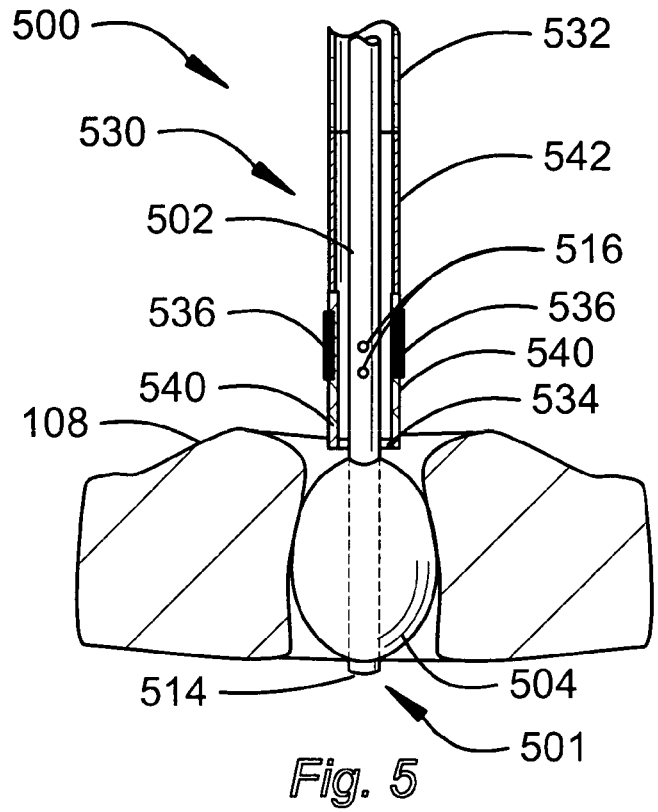
FIG. 5 is a side view showing a combination ablation and diversion catheter assembly according to an embodiment of the present invention.

The catheter assembly 500 shown in FIG. 5 includes an inner catheter 501 that includes occlusion and diversion features. The inner catheter 501 includes an elongated body 502, occlusion balloon 504, and distal ports 514 in fluid connection with proximal ports 516. These features of the inner catheter 501 can be constructed using techniques and materials similar to those described for the diverting catheter 100.

The catheter assembly 500 includes an outer catheter 530 that can provide ablation and/or cryogenic treatments. The outer catheter 530 includes a sheath 532 that is located over the elongated body 502 of the inner catheter 501. The outer catheter 530 may be fixably attached to the inner catheter 501, such that both catheters 530, 501 can be concurrently advanced into position during the procedure. Alternatively, the catheters 530, 501 may be slidably coupled so that each catheter 530, 501 can be advanced separately during the procedure.

The outer catheter 530 contains tissue treatment components such as cryogenic elements (e.g. tubes) or, as shown, an arrangement of electrodes 536. The electrodes 536 may also be used for other purposes such as electrophysiological mapping. The electrodes 536 are electrically coupled to electrical conductors (not shown) that extend to a proximal part of the catheter assembly and are used to deliver electrical power to the electrodes 536. In the illustrated configuration, the arrangement of electrodes 536 are "folded" such that the electrodes 536 substantially conform to an outer surface of the sheath 532 and/or inner catheter 501. In the folded configuration, the outer catheter 530 presents a minimal profile that is suitable for being introduced through mediate access vessels.

The catheter assembly 500 may include a stop member 534 that provides a mechanical coupling or engagement location between the inner and outer catheters 501, 530. The stop member 534 is fixably attached to one or both of the inner and outer catheters 501, 530 so that the outer catheter 530 cannot slide distally past the stop member 534. The stop member 534 assists in deploying of the outer catheter 530 to contact cardiac tissue during ablation procedures.

Figure 6:
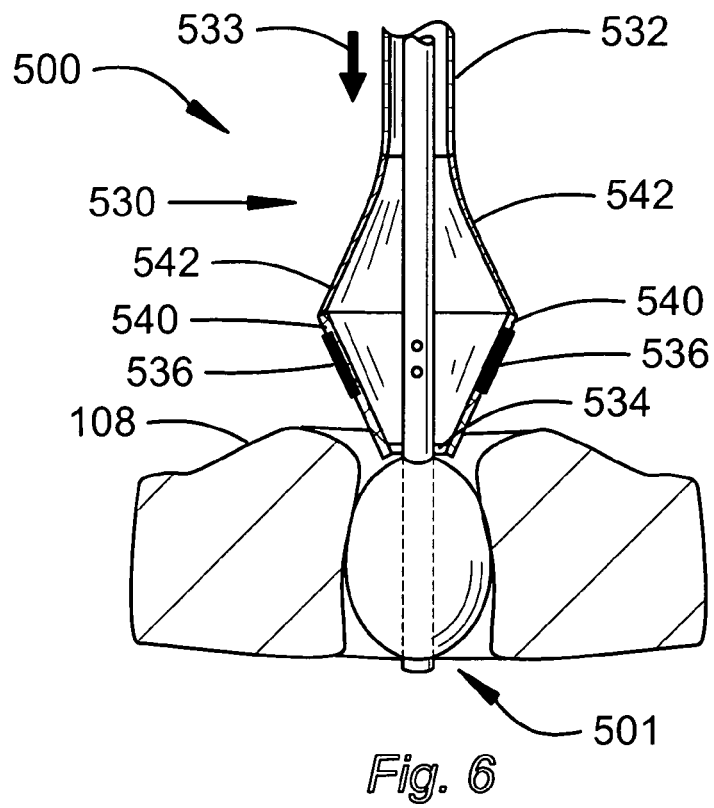
FIG. 6 is a side view of the catheter assembly of FIG. 5 in a partially deployed configuration.
Figure 7:
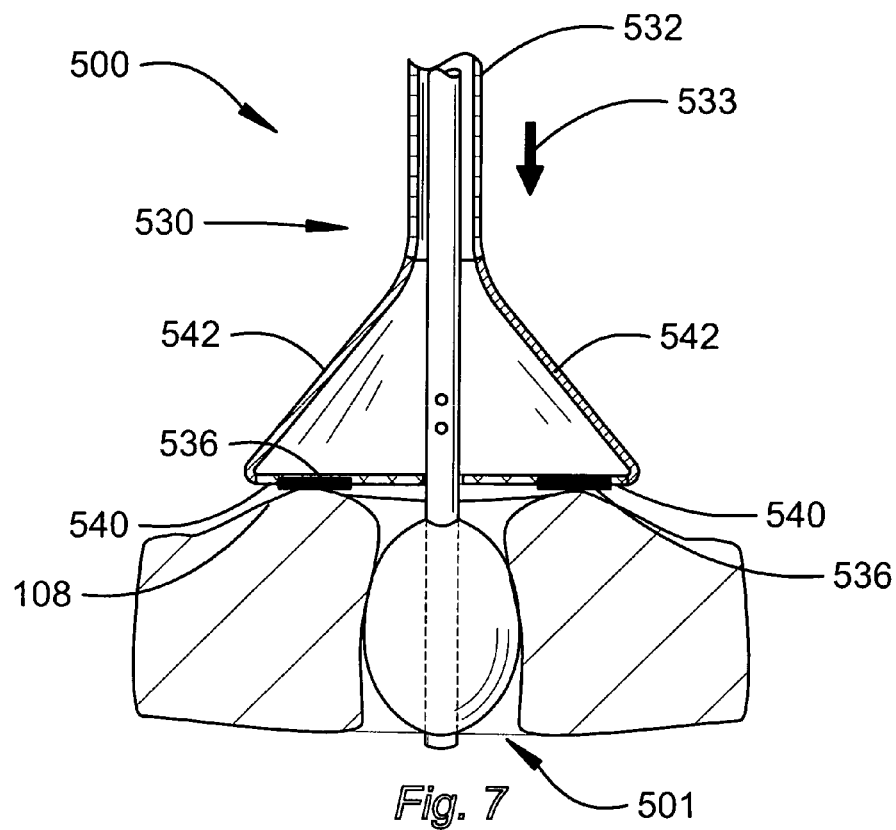
FIG. 7 is a side view of the catheter assembly of FIG. 5 in a fully deployed configuration.

FIGS. 6 and 7 illustrate an example of how the outer catheter 530 may be deployed so that the electrodes 536 are in contact with the ostium 108 or other cardiac surface. As shown in FIG. 6, deploying the outer catheter 530 involves pushing the sheath 532 against the stop member 534 in the direction indicated by the arrow 533. This will cause the one or more mounting members 540 and ribs 542 to fold outwardly so that an outer surface of the mounting members 540 moves toward the cardiac surface. The mounting members 540 include ablative electrodes 536 or cryogenic elements mounted on an outer surface of the members 540. The outer catheter 530 is configured so that deployment of the mounting members 540 positions the electrodes 536 to at least partially conform to a cardiac surface such as the ostium 108.

In FIG. 7, the outer catheter 530 has been pushed further in the direction of the arrow 533 so that the catheter 530 is in a deployed configuration. The deployed shape of the mounting members 540 roughly conforms to the ostium surface 108 so that the electrodes 536 are close to (and preferably in contact with) the surface 108. Once the outer catheter 530 is moved to the deployed configuration, treatment can be applied to the cardiac surface 108. After treatment is complete, the outer catheter 530 can be retracted to the folded configuration shown in FIG. 5. The outer catheter 530 can then be removed separately or together with the inner catheter 501.

Figure 8:
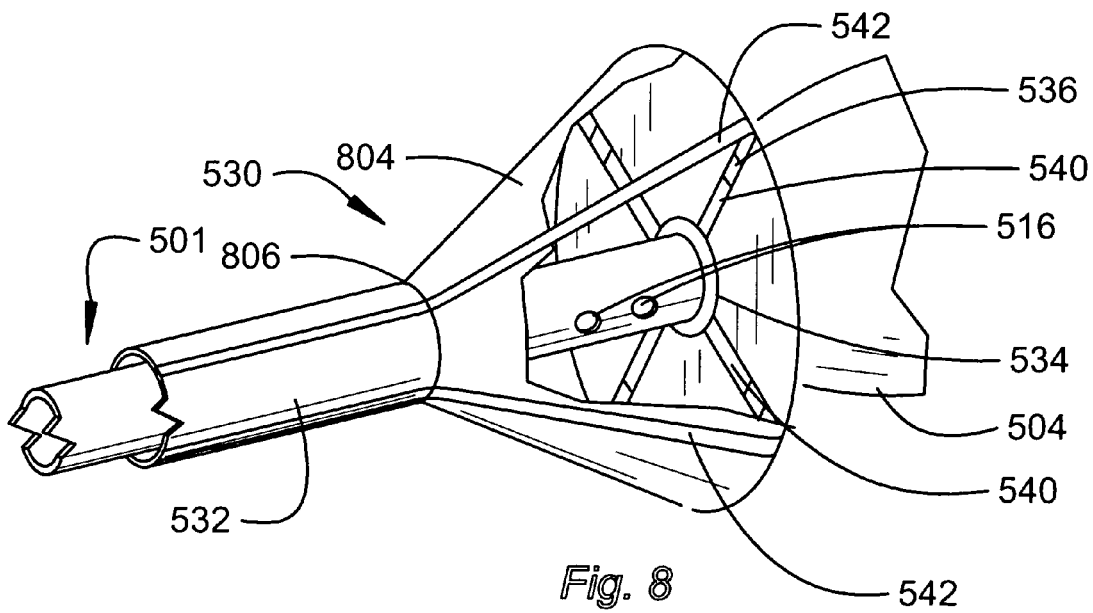
FIG. 8 is a perspective view of a combination ablation and diversion catheter assembly according to an embodiment of the present invention.

A perspective view of the outer catheter 530 in a deployed configuration is shown in FIG. 8. The mounting members 540 in this example include four elongated legs, although any number and shape of members 540 may be used. The mounting members 540 are hingably attached to four ribs 542. A webbing 804 is joined between the ribs 542 and is configured to stretch as the outer catheter 530 is deployed. The webbing 804 may also be attached between mounting members 540. The webbing 804 may be fabricated from a porous material or include voids that allow fluid to pass through. In this way, blood can flow between the proximal ports 516 and the surrounding circulatory system.

The webbing 804 and ribs 542 may be restrained at an anchor section 806. The anchor section 806 holds the proximal parts of the webbing 804 and ribs 802, allowing the ribs 802 to rotate outward but preventing any further spreading of the sheath 532. The anchor section 806 may be formed by adding a ring of additional material for support, or may include a natural stiffness transition point formed by attaching relatively flexible ribs 542 and/or webbing 804 to a relatively rigid sheath 532.

Figure 9:
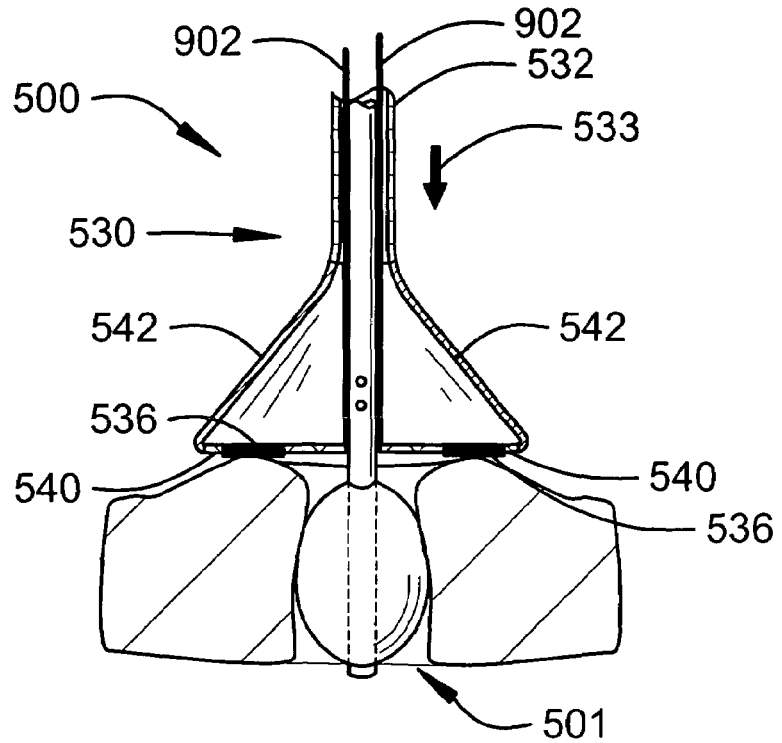
FIG. 9 is a side view showing an alternate configuration combination ablation and diversion catheter assembly according to an embodiment of the present invention.

It will be appreciated that alternate arrangements of the outer catheter 530 may be devised to deploy mounting members 540 and/or electrodes 536 so that the electrodes 536 are in contact with a cardiac surface. One example is shown in FIG. 9, where one or more tendons 902 are attached to a distal part of the mounting members 540 in lieu of the stop member 534. These tendons 902 can be pulled from a proximal end of the assembly 500 while pushing the outer sheath 532 in the direction indicated by the arrow 533. The tendons 902 in this example can be used to create buckling forces similar to that created by the stop member 534.

Figure 10:
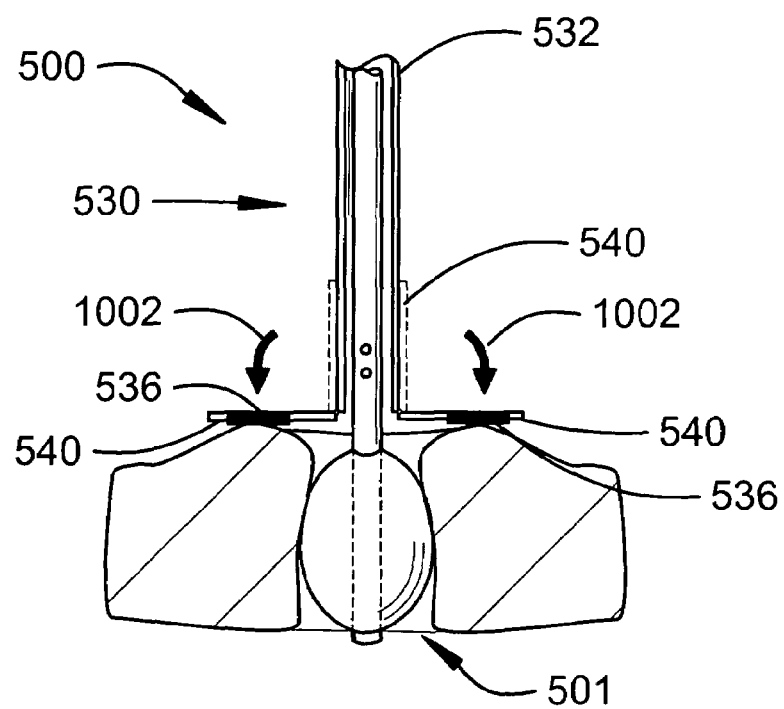
FIG. 10 is a side view showing another configuration of a combination ablation and diversion catheter assembly according to an embodiment of the present invention.

In another example, the folding structure that is formed by assembling the mounting members 540 and ribs 542 may be formed by a single molded member that assumes a shape similar to that shown in FIGS. 7, 8, and 9 when deployed. Alternatively, as shown in FIG. 10, the mounting members 540 may be distally hinged to the sheath 532. In this arrangement, the mounting members 540 move from a folded configuration (shown in dashed line) to the deployed configuration by rotating in the direction indicated by the arrows 1002.

The mounting members 540 shown in FIG. 10 may be deployed manually through such mechanisms as tendons or hydraulic actuators. The mounting members 540 may also include a spring (not shown) that automatically pushes the mounting members 540 to the deployed configuration. The spring may be manually actuated (e.g. a tendon operated release) or automatically actuated, such as by use of a superelastic member (e.g., nitinol wire) that changes shape based on body temperature.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A catheter for diverting blood flow through a cardiac vessel during ablation, comprising:
    a catheter body having a proximal end and a distal end;
    an inflation lumen in fluid connection with an inflation mechanism situated proximate the proximal end of the catheter body;
    a diversion balloon mounted at the distal end of the catheter body and inflatable to at least partially block blood flow through the cardiac vessel;
    one or more distal ports provided on the catheter body distal to the diversion balloon;
    one or more proximal ports provided on the catheter body proximal to the diversion balloon, wherein the proximal ports are in fluid connection with the distal ports so that a flow of blood through the cardiac vessel is directed via the distal and proximal ports so as to divert blood flow from a cardiac surface intended for ablation;
    an inner member slidable within the catheter body configured to selectively block blood flow through one or more of the one or more proximal ports and control blood flow;

an arrangement of ablation electrodes deployable from a folded configuration, the arrangement of ablation electrodes configured to substantially conform to an exterior surface of the catheter body in an un-deployed folded configuration and slide relative to the catheter body to unfold from the exterior surface of the catheter body and ablate the cardiac surface in a deployed configuration; and a sheath disposed around the catheter body, wherein distal motion of the sheath relative to the catheter body deploys the arrangement of ablation electrodes to the deployed configuration.

2. The catheter of claim 1, wherein the proximal ports are configured to divert a majority of the flow of blood through the cardiac vessel away from the cardiac surface intended for ablation.

3. The catheter of claim 1, wherein the arrangement of ablation electrodes comprises a plurality of ablation electrodes configured to be arrayed around the catheter body and conform to an ostium shape in the deployed configuration.

4. The catheter of claim 1, further comprising one or more mounting members attached to, and supporting, the arrangement of ablation electrodes, and a stop member fixably attached to one or both of the catheter body and the sheath, wherein the catheter is configured such that distal motion of the sheath relative to the catheter body engages the stop member with the one or more mounting members to fold outward the one or more mounting members and deploy the arrangement of ablation electrodes to the deployed configuration.

5. The catheter of claim 1, wherein the diversion balloon, when seated partially within the cardiac vessel, is configured to prevent the arrangement of ablation electrodes from entering the cardiac vessel.

6. The catheter of claim 1, further comprising a steering mechanism, wherein the distal end of the catheter body is deflectable by actuation of the steering mechanism at the proximal end of the catheter body to steer the catheter in a desired direction.

7. The catheter of claim 6, wherein the steering mechanism comprises a steering tendon connected to an anchor member positioned at a distal portion of the catheter, the steering mechanism providing uni-directional steering of the catheter.

8. The catheter of claim 1, wherein the one or more proximal ports are located at a distance proximal to the arrangement of ablation electrodes, and the diversion balloon blocks fluid flow, sufficient to negate local cooling effects of fluid flowing through the cardiac vessel during ablation.

9. The catheter of claim 1, wherein the size and number of distal and proximal ports are sufficient to divert a majority of the flow of blood through the cardiac vessel away from the cardiac surface intended for ablation.

10. The catheter of claim 1, wherein the catheter further comprises a plurality of mounting members attached to, and supporting, the arrangement of ablation electrodes and porous webbing joining the plurality of mounting members, and wherein the catheter is configured to allow fluid to flow through the porous webbing and the one or more proximal ports.

11. The catheter of claim 1, wherein the catheter further comprises one or more mounting members attached to, and supporting, the arrangement of ablation electrodes, and one or more tendons attached to the one or more mounting members, wherein coordinated distal motion of the sheath relative to the catheter body and proximally directed tension on the one or more mounting members provided by the one or more tendons deploys the arrangement of ablation electrodes to the deployed configuration.

12. A catheter for diverting blood flow through a cardiac vessel during ablation, comprising:

a catheter body having a proximal end, an exterior surface, and a distal end;

an inflation lumen in fluid connection with an inflation mechanism situated proximate the proximal end of the catheter body;

a diversion balloon mounted at the distal end of the catheter body and inflatable to at least partially block blood flow through the cardiac vessel;

one or more distal ports provided on the catheter body distal to the diversion balloon;

one or more proximal ports provided on the catheter body proximal to the diversion balloon, wherein the proximal ports are in fluid connection with the distal ports so that a flow of blood through the cardiac vessel is directed via the distal and proximal ports so as to divert the flow of blood from a cardiac surface intended for ablation;

one or more electrical conductors disposed along the catheter body and extending from the proximal end of the catheter body to at least a location proximate the diversion balloon;

an arrangement of ablation electrodes supported by the catheter body distal of the one or more proximal ports, the arrangement of ablation electrodes configured to substantially conform to the exterior surface of the catheter body in a folded configuration and slide relative to the catheter body to unfold from the exterior surface of the catheter body in a deployed configuration, the ablation electrodes electrically coupled to the one or more electrical conductors, the arrangement of electrodes operable for one or both of mapping and ablating a cardiac surface in the deployed configuration while the distal and proximal ports divert blood flow away from the cardiac surface; and a sheath disposed along the catheter body to which the arrangement of electrodes is coupled, wherein distal motion of the sheath relative to the catheter body deploys the arrangement of ablation electrodes to the deployed configuration.

13. The catheter of claim 12, wherein the arrangement of electrodes is configured for RF (radio frequency) ablation of the cardiac surface.

14. The catheter of claim 12, wherein the arrangement of electrodes is configured for microwave ablation of the cardiac surface.

15. The catheter of claim 12, wherein the catheter is configured such that at least a portion of the arrangement of electrodes is proximal relative to the one or more proximal ports when the arrangement of electrodes is in the folded configuration and the portion is distal relative to the one or more proximal ports when the arrangement is in the deployed configuration.

16. The catheter of claim 12, further comprising an inner dam situated within the catheter body proximal of the proximal ports, the inner dam blocking the flow of blood into the catheter body beyond the inner dam.

17. The catheter of claim 12, wherein the one or more proximal ports are located at a distance proximal to the arrangement of ablation electrodes in the deployed configuration, and the diversion balloon blocks fluid flow, sufficient to negate local cooling effects of fluid flowing through the cardiac vessel during ablation.

18. The catheter of claim 12, wherein the catheter further comprises one or more mounting members attached to, and supporting, the arrangement of ablation electrodes, and a stop member fixably attached to one or both of the catheter body and the sheath, the catheter configured such that distal motion of the sheath relative to the catheter body engages the stop member and the one or more mounting members to fold outward the one or more mounting members and deploy the arrangement of ablation electrodes to the deployed configuration.

19. The catheter of claim 12, wherein the catheter further comprises one or more mounting members attached to, and supporting, the arrangement of ablation electrodes, and one or more tendons attached to the one or more mounting members, wherein coordinated distal motion of the sheath relative to the catheter body and proximally directed tension on the one or more mounting members provided by the one or more tendons deploys the arrangement of ablation electrodes to the deployed configuration.

20. A cardiac ablation catheter for ablating a cardiac surface and diverting blood flow through a cardiac vessel during ablation, comprising:
   a catheter body having an exterior surface, a proximal end and a distal end;
   an inflation lumen in fluid connection with an inflation mechanism situated proximate the proximal end of the catheter body;
   a diversion balloon fixably mounted at the distal end of the catheter body and inflatable to at least partially block blood flow through the cardiac vessel;
   one or more distal ports provided on the catheter body distal to the diversion balloon;
   an arrangement of ablation electrodes configured to substantially conform to the exterior surface of the catheter body in a folded un-deployed configuration and slide relative to the catheter body to unfold from the exterior surface of the catheter body and ablate the cardiac surface in a deployed configuration;
   one or more proximal ports provided on the catheter body proximal to the diversion balloon and the distal end of the ablation catheter, wherein the proximal ports are in fluid connection with the distal ports so that a flow of blood through the cardiac vessel is directed via the distal and proximal ports so as to divert blood flow away from the cardiac surface; and
   a sheath disposed around the catheter body, wherein distal motion of the sheath relative to the catheter body deploys the arrangement of ablation electrodes to the deployed configuration.

21. The cardiac ablation catheter of claim 20, wherein the arrangement of ablation electrodes comprises a plurality of ablation electrodes configured to be arrayed around the catheter body and conform to an ostium shape in the deployed configuration.

22. The cardiac ablation catheter of claim 20, wherein the arrangement of ablation electrodes is configured to deliver a radio frequency ablation therapy.

23. The cardiac ablation catheter of claim 20, wherein the arrangement of ablation electrodes is configured to deliver a microwave ablation therapy.

24. The cardiac ablation catheter of claim 20, wherein the ablation catheter further comprises one or more mounting members attached to, and supporting, the arrangement of ablation electrodes, and a stop member fixably attached to one or both of the catheter body and the sheath, wherein distal motion of the sheath relative to the catheter body engages the stop member and the one or more mounting members to fold outward the one or more mounting members and deploy the arrangement of ablation electrodes to the deployed configuration.

25. The cardiac ablation catheter of claim 20, wherein the ablation catheter further comprises a plurality of mounting members attached to, and supporting, the arrangement of ablation electrodes and porous webbing joining the plurality of mounting members, the cardiac ablation catheter configured to allow fluid to flow through the porous webbing and the one or more proximal ports.

26. The cardiac ablation catheter of claim 20, wherein the ablation catheter further comprises a sheath disposed around the catheter body, one or more mounting members attached to, and supporting, the arrangement of ablation electrodes, and one or more tendons attached to the one or more mounting members, wherein coordinated distal motion of the sheath relative to the catheter body and proximally directed tension on the one or more mounting members provided by the one or more tendons deploys the arrangement of ablation electrodes to the deployed configuration.

* * * * *